United States Patent
Beller

(10) Patent No.: US 10,493,221 B2
(45) Date of Patent: Dec. 3, 2019

(54) POWDER INHALER AND POWDER INHALATION SET

(71) Applicant: Klaus-Dieter Beller, Kenzingen (DE)

(72) Inventor: Klaus-Dieter Beller, Kenzingen (DE)

( * ) Notice: Subject to any disclaimer, the term of this patent is extended or adjusted under 35 U.S.C. 154(b) by 560 days.

(21) Appl. No.: 15/115,675

(22) PCT Filed: Jan. 20, 2015

(86) PCT No.: PCT/EP2015/000089
§ 371 (c)(1),
(2) Date: Jul. 31, 2016

(87) PCT Pub. No.: WO2015/113742
PCT Pub. Date: Aug. 6, 2015

(65) Prior Publication Data
US 2016/0346490 A1 Dec. 1, 2016

(30) Foreign Application Priority Data

Jan. 30, 2014 (DE) .......................... 10 2014 001 072
Apr. 17, 2014 (DE) .......................... 10 2014 005 646

(51) Int. Cl.
*A61M 15/00* (2006.01)
*A61M 15/08* (2006.01)
*A61M 11/00* (2006.01)

(52) U.S. Cl.
CPC ...... *A61M 15/0041* (2014.02); *A61M 11/002* (2014.02); *A61M 15/0003* (2014.02);
(Continued)

(58) Field of Classification Search
CPC .............. A61M 15/00; A61M 15/0001; A61M 15/0003; A61M 15/0005;
(Continued)

(56) References Cited

U.S. PATENT DOCUMENTS 5,070,870 A * 12/1991 Pearce .............. A61M 15/0028
128/203.12
5,505,196 A 4/1996 Herold et al.
(Continued)

FOREIGN PATENT DOCUMENTS

DE 44 00 084 A1 7/1996
DE 10 2005 046 644 B3 7/2006
(Continued)

*Primary Examiner* — Joseph D. Boecker
(74) *Attorney, Agent, or Firm* — Gudrun E. Huckett

(57) ABSTRACT

The invention relates to a powder inhaler and to a powder inhaler set that contains the powder inhaler. The powder inhaler comprises two half-shells (3, 4), which are connected to each other by means of at least one film hinge and are formed as a single piece. In a joined arrangement, the two half-shells (3, 4) enclose an air inlet region, a powder deposition region and powder release region, and an outlet region, through which regions a fluid path extends, wherein at least one of the half-shells (3, 4) has at least one air inlet opening (8) in the air inlet region. Furthermore, one of the half-shells (3, 4) has at least one powder-accommodating recess (9) in the powder deposition region and powder release region, while the outlet region has at least one deagglomeration structure (17, 17') and an outlet for aerosol, which outlet is formed by the half-shells (3, 4).

24 Claims, 6 Drawing Sheets

(52) U.S. Cl.
CPC .... *A61M 15/0005* (2014.02); *A61M 15/0021* (2014.02); *A61M 15/0051* (2014.02); *A61M 15/08* (2013.01); *A61M 15/0043* (2014.02); *A61M 15/0063* (2014.02); *A61M 2202/064* (2013.01); *A61M 2205/586* (2013.01); *A61M 2206/14* (2013.01); *A61M 2207/00* (2013.01)

(58) Field of Classification Search
CPC ........ A61M 15/00021; A61M 15/0028; A61M 15/003; A61M 15/0033; A61M 15/0035; A61M 15/0038; A61M 15/004; A61M 15/0041; A61M 15/0043; A61M 15/0045; A61M 15/0051; A61M 15/006; A61M 15/0063; A61M 15/0086; A61M 15/08; A61M 11/002; A61M 2202/064; A61M 2206/14

See application file for complete search history.

(56) References Cited

U.S. PATENT DOCUMENTS

| | | | |
|---|---|---|---|
| 2002/0108611 A1* | 8/2002 | Johnston | A61M 15/0028 128/203.15 |
| 2006/0237010 A1* | 10/2006 | De Boer | A61M 15/0045 128/203.15 |
| 2013/0074841 A1* | 3/2013 | Von Schuckmann | A61M 15/0028 128/203.15 |
| 2014/0007875 A1* | 1/2014 | Aberg | A61M 15/0045 128/203.15 |
| 2014/0230817 A1* | 8/2014 | Richardson | A61M 15/0028 128/203.15 |
| 2015/0343159 A1* | 12/2015 | Farr | A61M 15/0026 128/203.15 |
| 2016/0151589 A1* | 6/2016 | Ohrt | A61M 15/0065 128/203.15 |
| 2017/0106154 A1* | 4/2017 | Herder | A61M 15/0028 |
| 2018/0280639 A1* | 10/2018 | Alexander | A61M 15/0086 |

FOREIGN PATENT DOCUMENTS

| | | | |
|---|---|---|---|
| DE | 10 2005 046 645 B3 | 7/2006 | |
| DE | 10 2009 041 664 A1 | 3/2011 | |
| DE | 20 2011 103 503 U1 | 12/2011 | |
| EP | 1 769 818 B1 | 4/2007 | |
| EP | 2 015 812 B1 | 1/2009 | |
| GB | 2 270 293 A | 3/1994 | |
| GB | 2460281 A | 11/2009 | |
| WO | 93/18811 | 9/1993 | |
| WO | 07/25086 | 7/1997 | |
| WO | WO-2008101992 A1 * | 8/2008 | ........ A61M 15/0028 |
| WO | 2011/154371 A1 | 12/2011 | |
| WO | WO-2012004485 A2 * | 1/2012 | ........ A61M 15/0028 |
| WO | 2013/036881 A2 | 3/2013 | |
| WO | WO-2015110832 A1 * | 7/2015 | .......... A61M 15/003 |

\* cited by examiner

POWDER INHALER AND POWDER INHALATION SET

BACKGROUND OF THE INVENTION

The invention concerns a powder inhaler and a powder inhalation set comprised of powder inhaler and blister element.

Powder inhalers for sublingual, nasal, and inhaling delivery of solid drugs or other substances in powder form are known. They can be designed as a propellant gas-free delivery devices that release an aerosol due to the inspiration process, respectively, a deep inhalation process. The energy for dispersing is obtained by the inspiration flow. In this context, the substance in powder form is contained in a storage container; special storage containers such as blisters are also known. Depending on the type of powder inhaler, the pure active ingredient is used or the active ingredient together with a carrier that is an innocuous excipient, for example, lactose or glucose for adhered active ingredient particles.

Known powder applicators or powder inhalers, depending on the design, may deliver up to three different types of powder. Such a powder inhaler is disclosed in EP 1 769 818 B1. Here, a propellant gas-free powder inhaler is used for inhaling delivery of solid drugs in powder form and enables also inhalation of a powder combination. This is achieved in that the powder inhaler comprises at least two storage containers in which different powders are stored separate from each other in several dosing units. The powders can be combined correspondingly and can be delivered through a common inhalation tube.

The powder inhaler disclosed in DE 10 2005 046 645 B3 is also provided for inhalation of two different powders and comprises also at least two storage containers for the different powders and makes it possible that they can be metered separate from each other in a dosing device and subsequently can be mixed with each other during inhalation.

The delivery even of different powders can be realized as an individual dose.

In order to improve the agglomeration degree and the emptying degree of the powder upon inhalation, the powder inhaler of DE 10 2005 046 644 B3 comprises in the inflow air channel a coil-shaped or spiral-shaped swirling device in order to swirl the air prior to supply to the powder and to obtain in this way a finer distribution of the powder in the air stream.

An inhaler for individual doses is known from DE 20 2011 103 503 U1. The powder inhaler for capsules described therein comprises a blade housing and a mouthpiece housing as well as a capsule carrier and several blades. The powder inhaler disclosed therein is intended to be used without complex preparation by an untrained user. The entire inhalation process is to be simply activated by a sliding movement; for this purpose, the device described therein has only two housing parts that are movable relative to each other and, due to their displacement relative to each other, initially the insertion opening for the capsule is closed and, in this way, the capsule is retained in a bore within the inhaler. In the interior of the inhaler, the capsule is then opened by suitably designed metallic blades.

EP 2 015 812 B1 discloses a powder inhaler for simultaneous delivery of several medicaments which are present in different depressions in an individual dose blister strip. For insertion of the blister, a mouthpiece of the powder inhaler is movably attached on a strip support. On the strip support of the powder inhaler, corresponding depressions for receiving the blister depressions are formed. A cover film of the inserted blister can be pulled off when the mouthpiece is closed in that the cover film is provided with a folded-over pulling tab that is projecting from the closed powder inhaler.

While most known inhalers are comprised of a plurality of components, which makes manufacture very expensive and complex, the above-mentioned inhaler of DE 20 2011 103503 U1 is already of a constructively simple design and can be manufactured inexpensively, but requires the use of blades and provides only a short simple transport path in order to transfer the powder from the capsule by means of inhaled air into a corresponding aerosol.

Based on this prior art, it is the object of the present invention to provide an inhaler that can be produced even more simply and remains hygienically safe even for multiple uses.

SUMMARY OF THE INVENTION

This object is solved with a powder inhaler comprising:
two half shells that are connected to each other by at least one film hinge and are formed as one piece, wherein both half shells in a joined arrangement enclose an air inlet area, a powder deposition and release area, and an outlet area through which a fluid path is extending, wherein
at least one of the half shells in the air inlet area comprises at least one air inlet opening,
in the powder deposition and release area, one of the half shells comprises at least one powder receiving depression, and
the outlet area comprises at least one de-agglomeration structure and an outlet for aerosol that is formed by the half shells.

Accordingly, there is the further object to provide a powder inhalation set that provides the inhaler together with active ingredients in direct ready to use form.

This object is solved by the powder inhalation set characterized in that it comprises a powder inhaler according to the invention and a blister element dimensioned for reception in the powder inhaler, wherein the blister element comprises a support film with at least one depression that is formed for receiving at least one active ingredient powder that is inhalable, and a cover plate that closes off the depression, wherein the at least one depression of the blister element in size and position is formed correspondingly for reception in the at least one powder receiving depression of the powder inhaler.

Further embodiments of the powder inhaler and of the powder inhalation set are disclosed in the dependent claims.

In a first embodiment of the powder inhaler, it comprises two half shells that are connected to each other by a film hinge and are formed as one piece. The two half shells enclose in a joined arrangement an air inlet area, a powder deposition and release area, and an outlet area, wherein a fluid path is extending through all these areas. In this context, one of the two half shells, in the powder deposition and release area, has at least one powder receiving depression into which the air stream that is supplied through the air inlet area is guided. Thereby the powder is completely conveyed out of the powder receiving depression and is already at least partially de-agglomerated. In the adjoining outlet area, one or more de-agglomeration structures are provided in order to de-agglomerate the powder further or even more finely and to prevent its deposition. At least one of the two half shells comprises in the air inlet area one or more air inlet openings and both half shells together form in the outlet area an outlet, respectively, an outlet opening. In this way, the two half shells in the joined state form a flow housing for the fluid path between the air inlet openings and the outlet so that the aerosol, which is formed upon inhalation in the powder deposition and release area from the powder to be inhaled, provided in the powder receiving depression, and from breathed-in air, can be inhaled through the outlet by the user. Advantageously, only a single component is required due to the hinged arrangement in order to form the powder inhaler by folding together the two half shells by means of the hinge, without this requiring further components or tools.

The powder inhaler can be manufactured advantageously as an injection molded part which makes manufacture particularly inexpensive. By means of the film hinge, the two components can remain captively connected to each other; they can be opened and closed which simplifies cleaning of the powder inhaler in case of multiple use. Also, the hinges assist in correct joining of the half shells by the user.

In order to be able to handle the powder inhaler properly and in order to be able to carry it along everywhere, it is advantageously comprised of two flat half shells with an elongate base that is substantially rectangular, possibly also trapezoidal or drop-shaped or oval. The shell is formed due to the rectangular or differently shaped base being rimmed by a wall or wall sections. The elongate half shells have therefore a longitudinal axis and its two ends comprise, on the one hand, the air inlet openings and, on the other hand, the outlet. At least one of the two half shells comprises on its wall section that is facing away from the outlet side the air inlet openings; advantageously, this is the half shell that does not carry the powder receiving depression. The reason for this is that the fluid path shaped for an optimal flow course is to be formed by means of the overall design.

"Fluid path" means in this context the path that is traveled first by the air alone and, after the entrainment of the powder by the air, by the aerosol. The aerosol is created when the portioned active ingredient in powder form that is present in the depression is entrained by inhaled air and along the following diffusor stretch is sufficiently mixed and dispersed. In order to form in the air supply area an ideal channel, preferably a venturi tube like channel, in which the fluid path is localized, at least one of the half shells, preferably however both of them, comprise several guiding webs which are extending all the way to the powder receptacle from the wall section where the air inlet openings are provided and/or from both wall sections adjoining next to the air inlet openings. In this context, the guiding webs of one half shell, relative to their height, extend all the way to the other half shell or, when both half shells comprise guide webs that thus form quasi guide web pairs, all the way to the guide webs of the other half shell so that two side by side neighboring guide webs (or side by side neighboring guide web pairs) form an air supply channel and delimit the fluid path in the air inlet area.

When an embodiment of the powder inhaler is provided by means of which at the same time two or more medicaments in powder form are to be inhaled and accordingly two or more powder receiving depressions are present in one of the half shells, the guide webs are arranged such that at least one air supply channel leads to each one of the powder receiving depressions, respectively.

Advantageously, the guide webs are arranged in a fan shape so that each air supply channel has a cross-section tapering toward the powder receiving depression. Moreover, it can be provided that in each air supply channel at least one air swirling structure is provided. Such an air swirling structure can be, for example, formed by vanes that project away from the guide webs into the supply air channel. These vanes are preferably arranged alternatingly on two guide webs, respectively, that are positioned in the half shells opposite each other and/or adjacent to each other, and form thus flow obstacles for an air stream flowing along the fluid path. The air is compressed by the funnel-shaped air supply channels and caused to rotate so that the air stream that is generated by inhalation has a highest speed and turbulence at the "funnel tip", i.e., when it reaches the powder receiving depression that, in turn, is framed on both sides by guide walls that extend from the outermost guide webs and guide the air stream from the air inlet area through the powder receiving depression. Due to the turbulent air stream, the powder is completely entrained out of the powder receiving depression. An optimal flow course is thus ensured independent of the type and depth of inhalation of the user.

The outlet of the powder inhaler can be formed as a mouthpiece, for example, like a spout, or for inhalation through the nose as a nosepiece, i.e., a curved nose tube.

At least one of the de-agglomeration structures provided in the outlet area can be formed by webs that are projecting into the fluid path and extend from oppositely positioned wall sections of at least one of the two half shells and that preferably extend transversely to the fluid path. Particularly preferred, these webs are arranged alternatingly on the wall sections in order to produce additional turbulence. Instead of the webs, in the outlet area also other flow obstacles can be provided, for example, extending radially to the fluid path and embodied to be approximately screw-shaped.

At least a further one of the de-agglomeration structures borders in the outlet area the powder deposition and release area and can be formed by a deflection web or several such structures that is/are arranged in one of the half shells, preferably the half shell that comprises the powder receiving depression.

The flow obstacles or de-agglomeration structures serve to break up and thus comminute, where necessary, larger powder particles during transport of the powder and entrainment by the air stream by means of the flow obstacles, respectively, the webs or the screw-shaped lamella. Moreover, in this way the active ingredient can be separated, where necessary, from a carrier substance. Further mechanical resistance elements of any shape, respectively, flow resistance elements, can be positioned as de-agglomeration devices in order to embody the fluid path so as to be tailored as needed and matched to the specifications of the medicament. Conceivable in this context are also, for example, wall-shaped or bollard-shaped structures that may also be arranged in a ring shape, or cyclone-type structures, or also structures arranged as an oval.

In principle, the outlet, no matter whether it is designed as a mouthpiece or embodied as a nose piece, can be provided with a cross-section that may be round or oval and that, across its total length, decreases or stays the same. Of course, also a polygonal cross-section is not precluded but is less suitable. It is expedient to embody the cross-section to be tapering all the way to the outlet location of the aerosol.

The overall configuration of the fluid path serves for optimal flow and acceleration of the inhaled air stream and improved entrainment and dispersion of the active ingredient in powder form. In particular, it is to be achieved that the powder contained in the powder receiving depression is completely removed therefrom with one inhalation.

The free configuration of the profile of the fluid path and the corresponding flow obstacles or de-agglomeration devices enable the adaptation of the inhaler for different active ingredients that are suitable for inspiration and can be in particular drugs. For example, dry drugs in powder form can be dispersed in the stream as particles of defined size.

The inhaler according to the invention is particularly hygienic in regard to handling due to its design and due to the possibility of opening and cleaning it. It is without blades, springs or levers. When producing and delivering powder aerosol, the adhesion and the friction in the inhaler play an important role. Adhesion and friction between active ingredient and inhaler can be overcome by a turbulence-generating fluid path course. Since the powder particles have the tendency to adhesively deposit on the inner inhaler surface, a suitable continuous fluid path course without complete flow reversal is therefore particularly preferred in order to avoid this. The flow obstacles in the air supply area and outlet area are designed to optimize the speed and turbulence in the guided air stream in order to achieve the best possible powder release and de-agglomeration which leads to improved inhalation performance.

In order to release an active ingredient contained in a depression of a blister element when the blister element is received with the depression in the powder receiving depression of the powder inhaler, a plunger can be provided in the half shell opposite the powder receiving depression which, by means of an elastic insert, is inserted in the half shell so that the plunger by pressure from the exterior can be moved at the location of the elastic insert in the direction toward the powder receiving depression(s) and upon release of the outer pressure, as a result of the restoring force of the elastic insert, can return into its initial position. The plunger in this context is embodied as a pricker, for example, as a star-shaped pricker with three, four or more edges so that the active ingredient depression of the blister element is perforated when the pricker is pushed in.

Moreover, at one of the half shells on a sidewall section at the level of the powder receiving depression a cutout can be provided whose width corresponds to the width of a blister element that is predetermined for insertion into the powder inhaler. The powder inhaler itself can be designed correspondingly so that it serves for receiving defined blister elements.

Expediently, the cutout can have a height that is higher than the height of the blister element. However, in this context this means the height of the blister film of support film and cover film and not the height of the medicament depression or capsule. Then, the second half shell, thus expediently the half shell that does not comprise the cutout, has a projection at the sidewall section which, in the joined arrangement of the half shells, is positioned above the cutout. The projection is designed to close off the cutout when an appropriate blister element is received in the powder inhaler, i.e., a part of the blister film is projecting through the cutout out of the powder inhaler. The cutout can be provided such that the inhaler is suited for right-handed persons or for left-handed persons.

By closing off the cutout after insertion of the blister element, it is prevented that at an undesirable location air can be sucked into the inhaler upon inhalation.

Moreover, the half shell that comprises the powder receiving depression comprises at least one stop element that serves for framing a blister element that is predetermined for reception in the powder inhaler. Therefore, the blister element when inserted cannot slide.

One embodiment provides that opening of the active ingredient depression of the blister element is not realized by perforation by means of a movable pricker but by pulling off the cover film. The latter projects by means of a folded-over pulling tab through the cutout out of the joined powder inhaler. In order for the active ingredient depression to remain positioned safely and correctly in the powder receiving depression upon pulling off the cover film by means of the pulling tab that is projecting out of the closed powder inhaler, both half shells can be provided at the sidewall sections at the level of the powder receiving depression opposite the cutout and the projection with a ribbing whose width corresponds approximately to the width of the blister element which is predetermined for insertion into the powder inhaler so that the blister element or a corresponding blister film section is held in place by the ribbed sidewall sections in the closed state of the powder inhaler.

Alternatively or in addition thereto, it can be provided that at the half shell that comprises the powder receptacle a projection, for example, a dome-shaped projection, is provided as an abutment and is designed to be brought into engagement with a corresponding recess of the blister element that is provided to be inserted into a powder inhaler according to the invention.

Finally, the one-piece powder inhaler can also be comprised of three half shells. In this context, the additional half shell can be attached, respectively injection-molded, by means of at least one hinge to one of the half shells, preferably that one without air inlets. This half shell has expediently also a base which corresponds to the base surface or the base of the half shells that from the flow housing. The third attached half shell serves, on the one hand, to be able to place the powder inhaler in a comfortable way into the hand and, on the other hand, the half shell with an appropriate size can be used to store at least one blister element therein. Of course, this half shell can also be designed such that several suitable blister elements can be accommodated.

It is not precluded that also further foldable elements, for example, yet another half shell can be linked by corresponding hinges to one of the described half shells as long as it is ensured that the air inlets are not closed off.

In the area of the powder receiving depression, at least one of the two half shells can be manufactured of transparent plastic material in order to enable viewing of the interior of the powder receiving depression and to thereby permit visual inspection whether the powder has been completely removed from the powder receiving depression after an inhalation process has been completed.

On the half shells suitable locking means for joining are provided; the configuration of such locking means is known to a person of skill in the art. The locking means can be provided on the appropriate edges of the half shells. Suitably, all of the half shells, this may be two, three, or even also four, are provided with locking means so that they can be simply locked with each other and coupled upon folding them together.

Further subject matter of the invention is a powder inhalation set that is comprised, on the one hand, of the powder inhaler according to the invention and, on the other hand, of a corresponding blister element that is dimensioned for reception in the powder inhaler. Such a blister element comprises a support plate or support film with a depression in which the powder is received, respectively, the active ingredient that can be inhaled. A matching blister element can also comprise two or more depressions with different active ingredient powders that are to be inhaled at the same time. The blister element comprises moreover a cover plate or cover film that closes off the depression(s) for as long as the powder is to be stored in the blister element. The depression(s) of the blister element is/are configured in regard to size and position for reception in the powder receiving depression(s) of the powder inhaler.

In order to release the powder by opening the depression of the blister element when the inhalation process is to be performed, the cover plate can be removed from the support plate and thus from the active ingredient depression in that the cover plate is formed, for example, with a foldable pulling tab which, with the blister element positioned in the powder inhaler, projects at the level of the powder receiving depression through the cutout in a sidewall section out of the powder inhaler and can be pulled off.

As disclosed above, for pulling off the cover film, a ribbing can be provided on the sidewall sections opposite the cutout as an abutment or a dome-shaped projection can be provided; as the case may be, the blister element with extended support film and cover film is used which, when the powder inhaler is folded closed, is secured between the ribbed portion or the blister element comprises a recess which is positioned relative to the active ingredient depression in accordance with the dome-shaped projection in relation to the powder receiving depression.

An alternative embodiment provides a simpler blister element that must not project with a section of the cover plate out of the powder inhaler but is only inserted with precise fit with the active ingredient depression into the powder receiving depression of the powder inhaler. Optionally, in this embodiment a capsule-like blister element or a specially designed capsule can be used also. Opening of the active ingredient depression is not realized here by removing the cover plate but by perforation thereof. A powder inhaler according to the invention which is designed for this is provided with a plunger that is embodied as a pricker and elastically movable relative to the powder receiving depression.

It can also be provided that a powder inhaler according to the invention is provided with both opening mechanisms so that both blister types can be opened.

BRIEF DESCRIPTION OF THE DRAWINGS

Further embodiments as well as some of the advantages that are associated with these and further embodiments will become more clear and easier to understand with the aid of the following detailed description referencing the attached figures. Elements or parts thereof which are substantially identical or similar can be provided with the same reference characters. The figures are only a schematic illustration of an embodiment of the invention. In this context, it is shown in:

FIG. 1a and FIG. 1b perspective views of powder inhalers according to the invention for inhaling delivery through the mouth in open state, comprising in

FIG. 1a) a ribbing

FIG. 1b) a dome-shaped projection as abutment;

DESCRIPTION OF PREFERRED EMBODIMENTS

The device according to the invention relates to a powder inhaler for inhaling delivery through mouth or nose of an active ingredient in powder form which is stored in a blister, wherein the active ingredient may be a medicament but also an active ingredient which is not necessarily defined as a medicament and which is inhaled by a person.

Figure 1A:
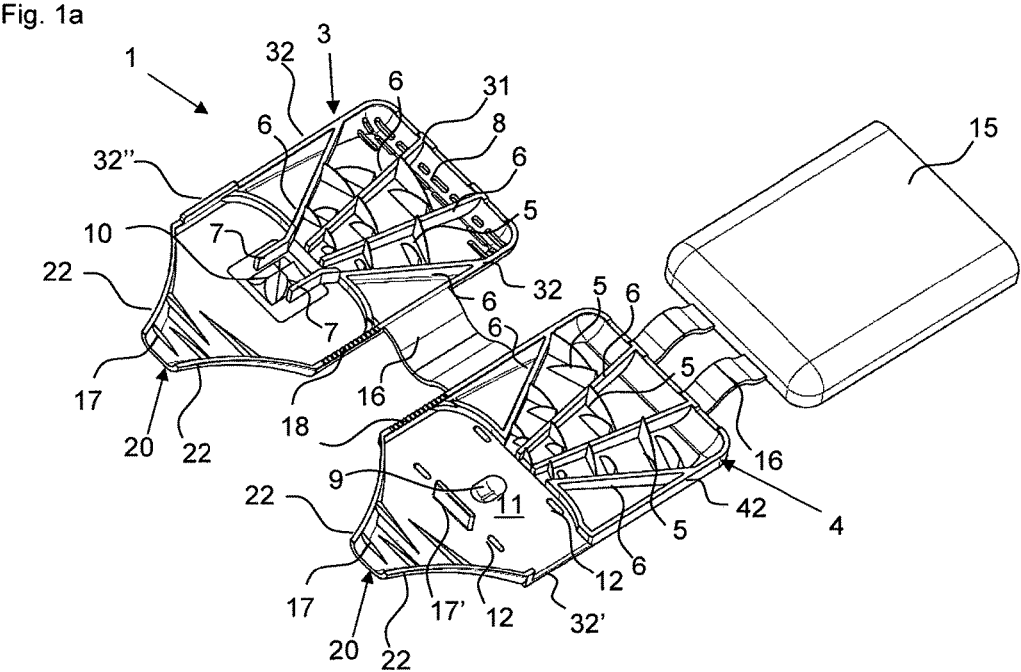
Figure 1B:
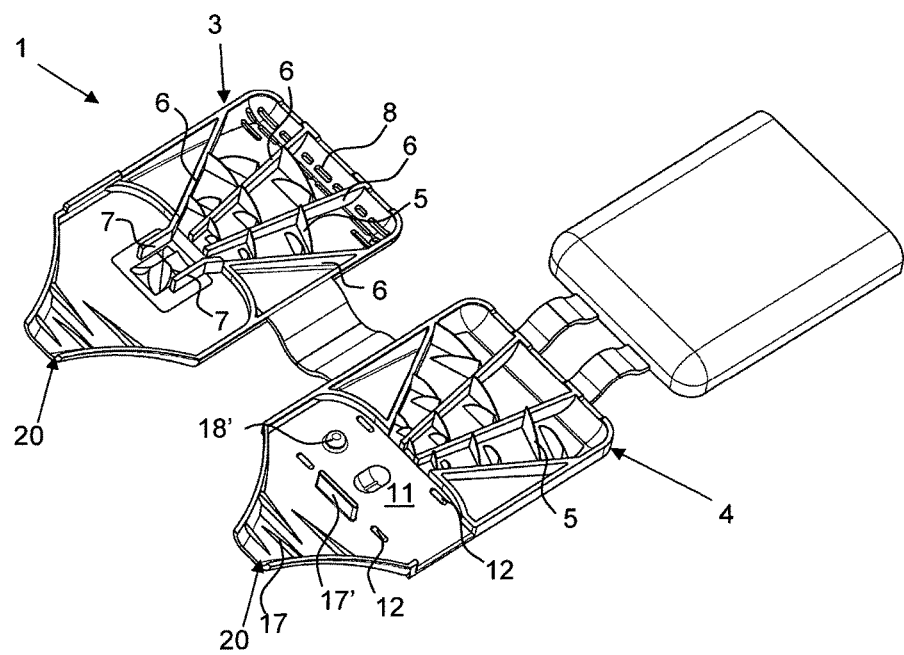
Figure 2A:
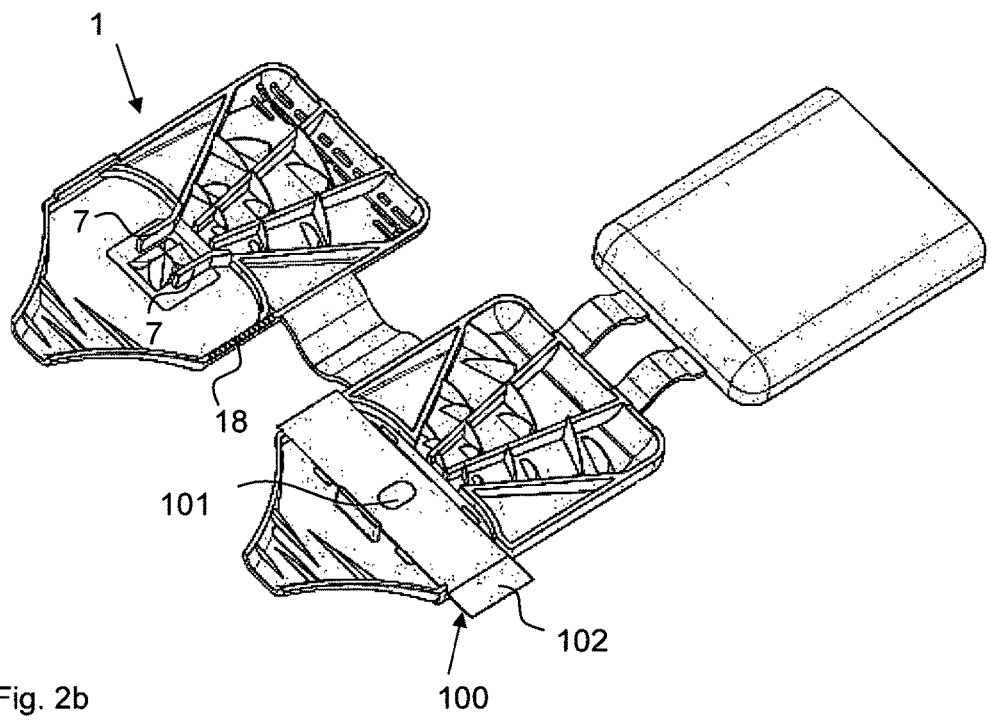
FIG. 2a and FIG. 2b views according to FIGS. 1a) and 1b) with inserted blister.
Figure 2B:
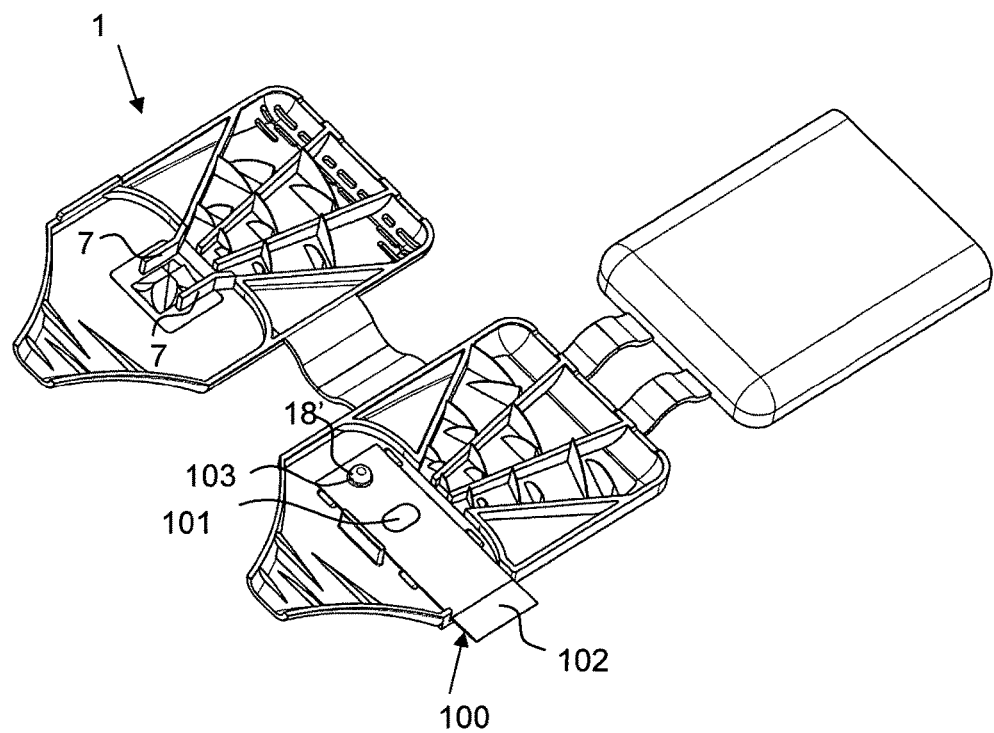
Figure 3:
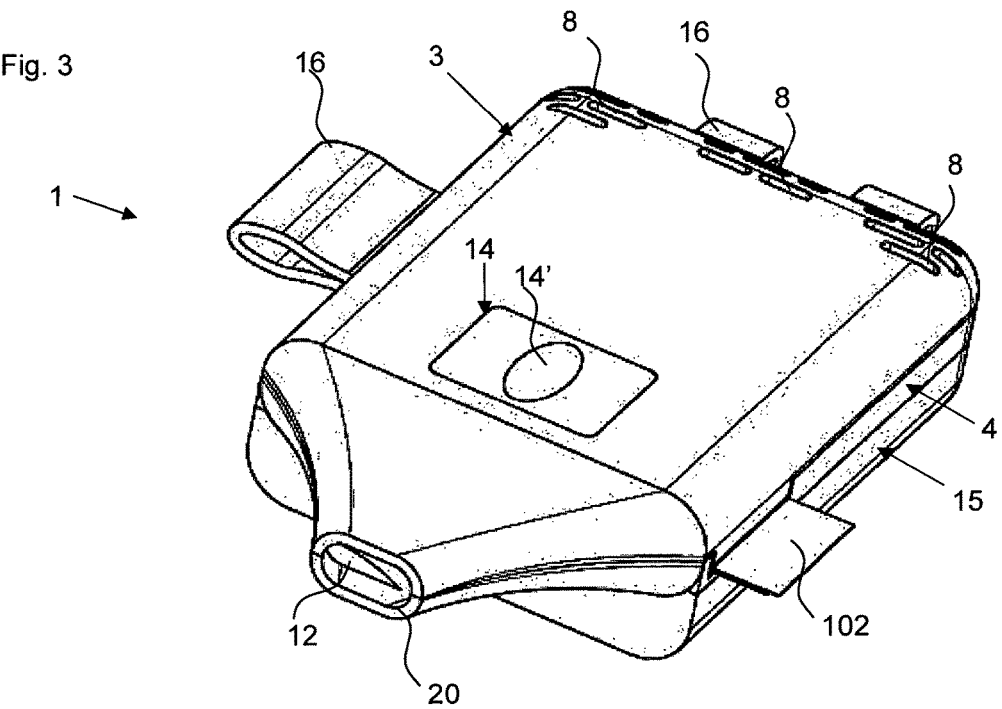
FIG. 3 a perspective view of the powder inhaler of FIG. 1a and FIG. 1b in closed state.
Figure 4:
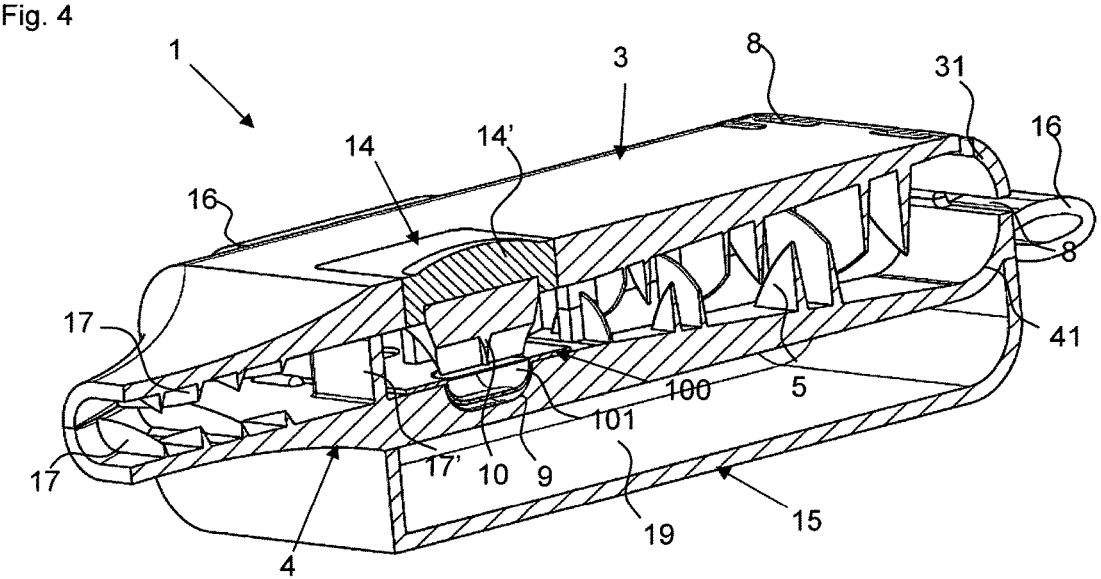
FIG. 4 a perspective longitudinal section of the powder inhaler of FIG. 3.
Figure 5:
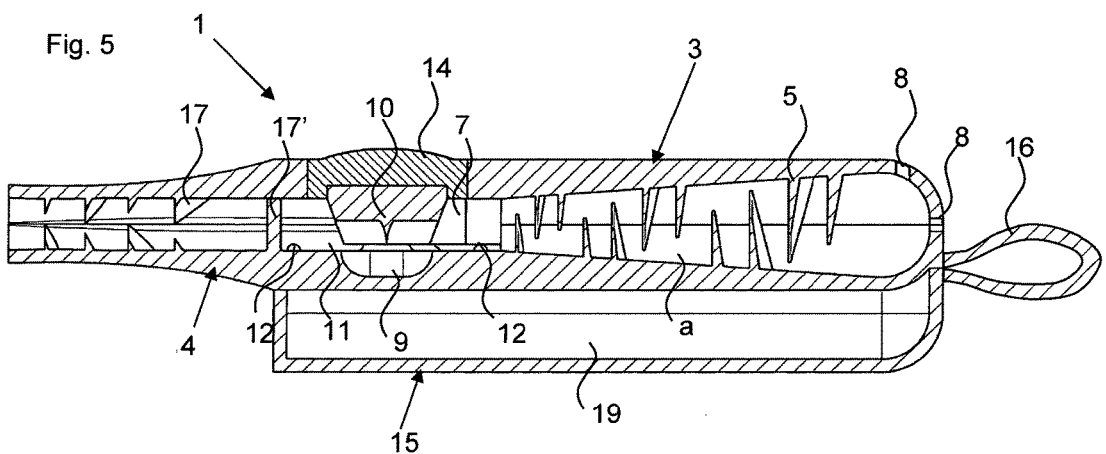
FIG. 5 a longitudinal section view of the closed powder inhaler without blister.
Figure 6:
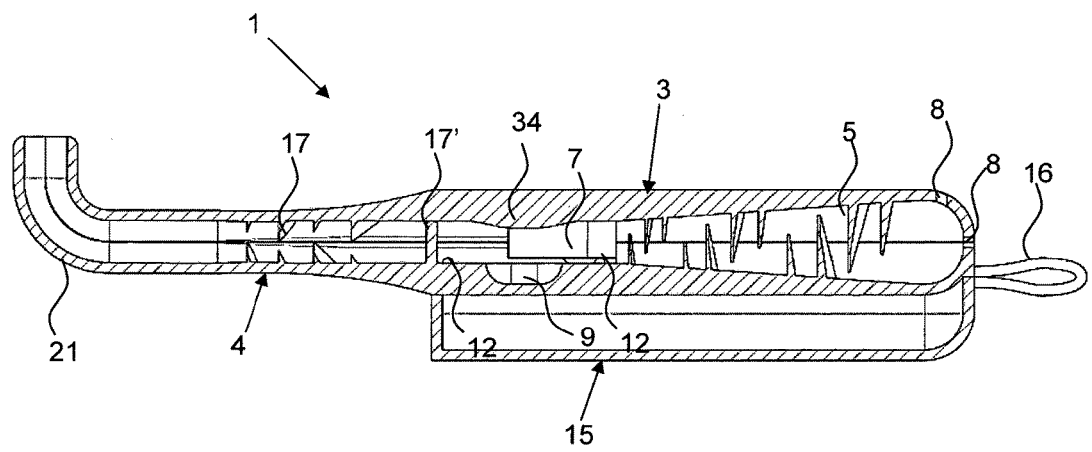
FIG. 6 a longitudinal section view of a further powder inhaler according to the invention for nasal delivery in closed state without blister.
Figure 7:
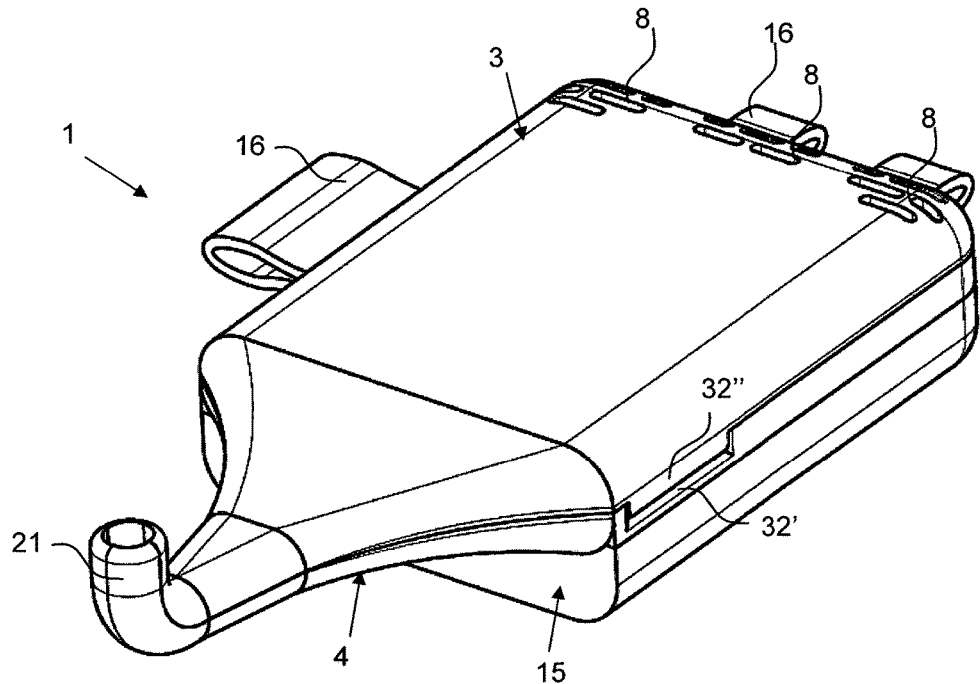
FIG. 7 a perspective view of the powder inhaler of FIG. 6.
Figure 8:
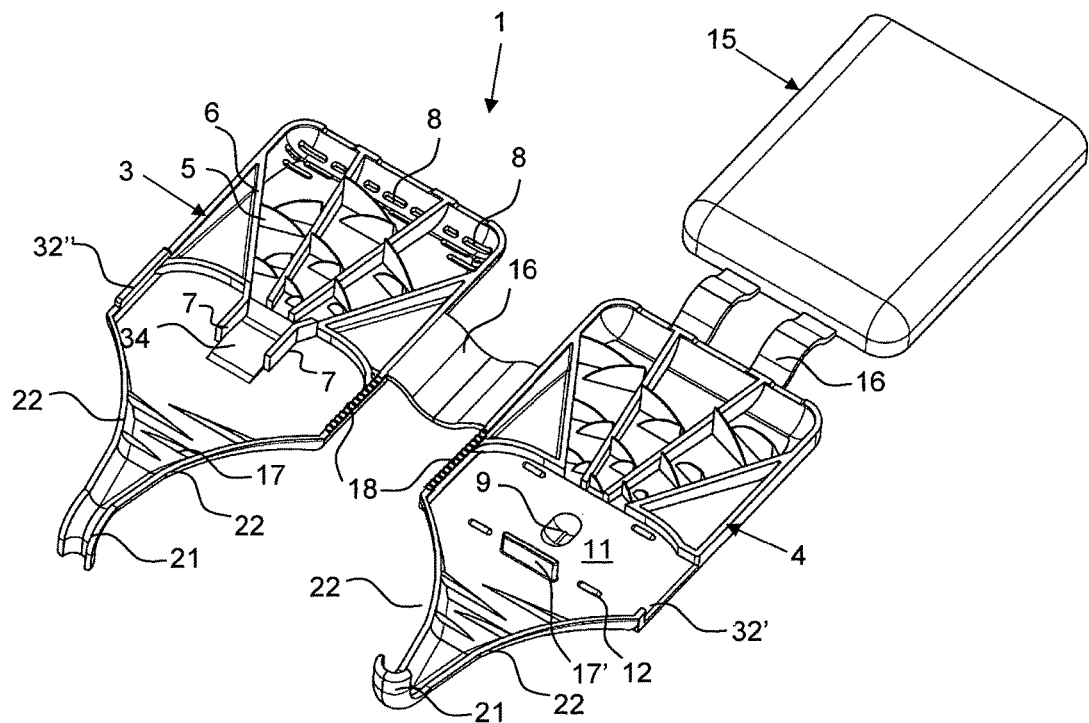
FIG. 8 a perspective view of the powder inhaler of FIGS. 6 and 7 in open state.
Figure 9:
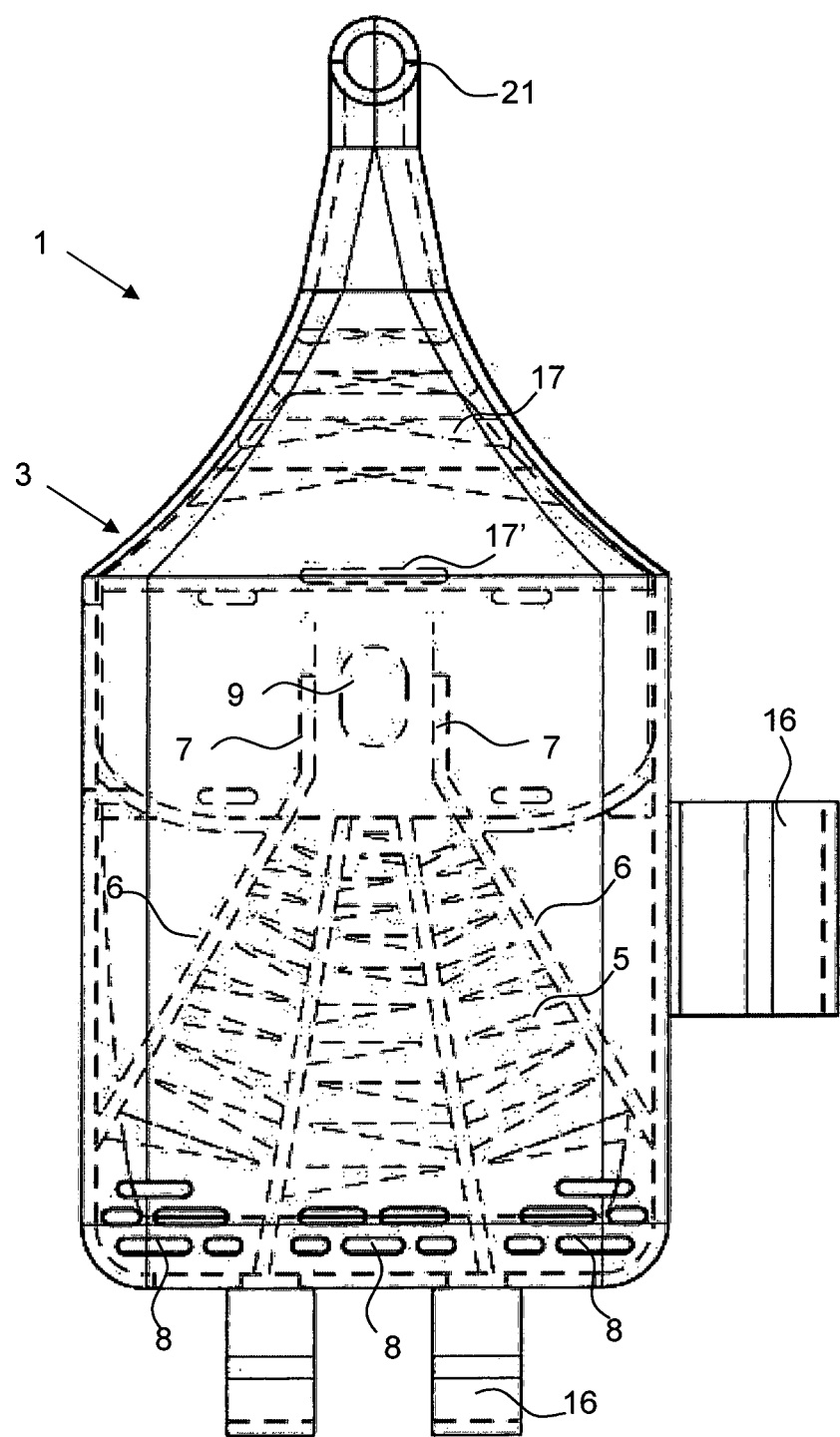
FIG. 9 a plan view of the powder inhaler of FIGS. 6 to 8.

FIGS. 1a) and b) show powder inhalers 1 according to the invention for inhaling delivery in open state, comprised of two half shells 3 and 4 which in the folded closed state form a ready to use powder inhaler. The two powder inhalers 1 differ only with regard to the embodiment of the abutment for holding the blister element when pulling off the cover film. In the illustrated form, the powder inhaler 1 can be produced advantageously quickly and inexpensively as one piece with a single tool by injection molding of plastic material, for example. In order to convert the powder inhaler 1 into the ready to use state, a blister element 100 is inserted at a location provided for this purpose(see FIGS. 2a, b). After folding closed the two half shells 3 and 4 and opening of the medicament depression 101 of the blister element 100, the powder inhaler 1 is ready to use (FIG. 3).

The powder inhaler 1 can be divided roughly into three partial areas:
- the outlet area with de-agglomeration structures 17, 17' which is formed as a mouthpiece in the embodiment illustrated in FIGS. 1 to 5,
- the air supply area which extends from the back wall 31 provided with air inlets 8, i.e., the wall present on the base of the half shell 3 and facing away from the outlet area, all the way to the blister chamber 11 and which comprises the funnel-shaped air supply channels separated by the guide webs 6, and
- the powder deposition and release area which comprises the blister chamber 11 with the powder receiving depression 9 in which a blister element 100 with an active ingredient depression 101 can be received.

The configuration according to the invention of the three partial areas ensures that, upon inhalation, an optimal air stream for delivery of the active ingredient, in the following also referred to as medicament, is formed, independent of the way the patient is inhaling. In this way, the medicament can be optimally inhaled and thereby best possible action achieved.

The air supply area in the examples illustrated in the figures is provided by three air supply channels that taper in the direction toward the powder receiving depression 9 and are delimited by guide webs 6 and into which through the air inlets 8 air is flowing in when the patient is inhaling through the mouth piece 20 received in the mouth. The air inlets 8 are provided in the back wall 31 of the half shell 3 as well as at the contact surface of the back walls 31, 41 between the two half shells 3, 4 (compare FIG. 4). In each air supply channel, air swirling structures in the form of vanes 5 (deflection vanes 5) are arranged and are each projecting from the guide webs 6 of both half shells 3, 4 into the channels. The tapering air supply channels and the deflection vanes 5 provide turbulence and increase the speed of the air supply stream prior to entering the powder receiving depression 9.

Of course, the number of the air supply channels in other embodiments, in particular also in embodiments with more than one powder receiving depression, can be varied.

For arranging the blister 100 (compare FIG. 2a) and b), the half shell 4 has in a sidewall 42 a cutout 32' through which the inserted blister 100 is extending with a folded over pulling tab 102 of the cover film of the blister element 100. This cutout 32' is air-tightly closed by the projection 32" at the other half shell 3. The active ingredient depression 101 of the blister element 100, which can also be referred to as capsule, is located in the depression 9 formed in the half shell 4. While FIGS. 1a) and 2a) show an embodiment in which the blister element 100 is secured by ribbing 18 in the sidewalls 32, 42 relative to the cutout 32' and the projection 32" in the half shells 3, 4, when the powder inhaler 1 is closed, the abutment of the powder inhaler 1 in FIGS. 1b) and 2b) is formed by a dome-shaped projection 18' positioned adjacent to the powder receiving depression 9 and penetrating an appropriately positioned opening 103 of the blister element 100 and ensuring a securing action immobilizing the blister element 20 in the powder inhaler 1 when, for opening the active ingredient depression 101, one pulls at the section 102 of the cover film of the blister element 100 (compare FIG. 3) that is projecting from the powder inhaler 1.

For a position-precise arrangement of the blister element 100, moreover the stops 12 are provided in the half shell 4. The deflection web 17' functioning as a de-agglomeration device further assists in positioning the blister element 100.

For guiding the air stream through the active ingredient depression 101 that is inserted into powder receiving depression 101 and is opened, guide walls 7 (FIG. 1) are provided at an appropriate location in the half shell 3 and extend from the outermost guide webs 6, when the powder inhaler 1 is closed, all the way to the blister element 100 so that the air stream is guided out of the air inlet area through the powder receiving depression 9 and the open powder-filled depression 101 of the blister element 100 arranged therein.

The outlet area adjoins the blister chamber 11 and the now formed aerosol of air and medicament powder is delivered via it. The blister chamber 11 is delimited relative to the outlet area by the de-agglomeration device 17' which, together with the further de-agglomeration devices 17, prevents the air stream laden with the active ingredient from directly reaching the outlet in that turbulences are generated by deflections in order to de-agglomerate the powder and to prevent renewed deposition or agglomeration of the medicament powder. However, downstream of the passage narrowly delimited by the guide walls 7, a cross-sectional widening, effected by the powder receiving depression upstream of the deflection by de-agglomeration device 17', first causes a reduction of the flow speed and creates in this way a spacer effect, i.e., the active ingredient particles are distributed uniformly within the air stream. Subsequently, the de-agglomeration of the active ingredient particles is enhanced by the vane-shaped webs 17 projecting into the fluid path as de-agglomeration devices in the tapering mouthpiece 20. Generally, de-agglomeration devices can also be formed by other structures than the here illustrated webs 17, 17', for example, cyclones or bollards, as long as the structures ensure swirling of the air stream after having passed the powder receiving depression.

In an advantageous simple way, the powder inhaler 1 comprised of the two half shells 3, 4 that are connected by a film hinge 16 can be transferred into the ready to use state by folding after insertion of the blister element 100 in the open state. Due to the flat configuration, the powder inhaler 1 can be carried along in a simple and comfortable way without pockets on clothing bulging excessively. When administration of the medicament is required, pulling off the end section 102 for opening the powder depression 101 or penetration of the cover film is required and the medicament can be inhaled.

In order to be able to carry along in a simple way additional blisters, in the present example it is provided that a further half shell 15 is connected by means of film hinges 16 to the half shell 4. Generally, it is however also possible that this storage half shelf 15 is arranged also on the half shell 3. In this case, the air inlets 8, which in the illustrated example are present at the back wall 31 of the half shell 3, should be arranged in the other half shell 4. When the storage half shell 15 is pivoted onto the half shell 4, as shown in FIG. 4, a storage space 19 is delimited in which, for example, additional blisters can be carried along. Moreover, the gripping ergonomics when holding the powder inhaler 1 can be improved by the storage half shell 15.

In an embodiment that is not illustrated, in place of a third half shell a swirling structure, or several swirling structures, can be connected by means of a hinge and can positioned by folding into the air channel/air channels.

As can be seen in FIGS. 1 to 5, an alternative mechanisms, comprising a plunger 10 embodied as a pricker, for opening the active ingredient depression 101 of the blister element 100 can be provided instead of pulling off the cover film. The pricker 10 is secured by an elastic insert 14 in the half shell 3 wherein the elastic insert has an outwardly curved portion 14' which is indicating to the user the pressure point that must be actuated in order to penetrate the cover film of the blister depression 101 of the inserted blister element 100 with the pricker 10. After actuation of the pressure point by the user, the pricker 10 is returned again by the elastic insert 14 into its initial position. Advantageously, the plunger 10 in this position guides the turbulent air stream out of the air inlet area into the powder receiving depression 9, or the active ingredient depression 101 contained therein. The manufacture of this powder inhaler can be realized in that first the elastic insert 14 is injection molded and the remaining inhaler shape is then injection molded onto the elastic insert 14, or vice versa, for example, by a 2C injection molding process.

It is possible that the powder inhaler according to the invention comprises both opening mechanisms, i.e., a plunger and an abutment, comprised of ribbing or bollards, in order to be able to open different blister types; however, it may also be sufficient when a powder inhaler according to the invention comprises only one of the alternatives.

As can be seen in the sectioned side view of FIG. 5, the air supply channels taper not only in regard to their width but also in regard to their height in the direction toward the blister chamber 11 wherein the wall thickness of the half shells 3 and 4 increases correspondingly. The vanes 5 projecting into the air inlet channels provide for a worm-shaped or spiral-shaped path which causes the airstream to rotate (similar to a tornado). Due to the rotation, centrifugal forces and pressure phenomena are generated which are important for the complete entrainment of the powder out of the powder receiving depression 9. Particularly effective in this context are oppositely oriented swirls that can be obtained, for example, by the central and right air supply channel in FIG. 9.

The additional FIGS. 6 to 9 represent a further exemplary embodiment of the powder inhaler 1 according to the invention that is provided for nasal delivery. Therefore, the outlet is designed as a curved nose tube 21. In other respects, this powder inhaler 1 for nasal delivery corresponds mostly in configuration and function to the afore described powder inhaler 1 for inhaling delivery through the mouth, however, without the movable plunger. In this powder inhaler, opening of the active ingredient depression of the blister element is thus performed by pulling off the cover plate. Opposite the powder receiving depression 9, the half shell 3 has a thicker wall portion 34 between the guide walls 7 in order to avoid at this location a cross-sectional increase and to guide the turbulent air stream out of the air supply area into the powder receiving depression 9 or to the active ingredient depression received therein.

Of course, a powder inhaler with nose piece can also be embodied with an elastically supported plunger for perforation of the blister. Generally, the elements (ribbing or projection) serving as abutments for the pulling off action, as well as the cutout and the corresponding projection in the sidewalls can be eliminated when only the plunger is to be used for opening the blister.

Finally, it is not precluded that a powder inhaler according to the invention can also can be used without blister element in that, in the open state of the powder inhaler, a powder dose is directly introduced into the powder receiving depression and inhaled immediately after folding together the half shells.

LIST OF REFERENCE NUMERALS 1 powder inhaler
3 first half shell
4 second half shell
5 swirling structure, vane
6 guide web
7 guide wall
8 air inlet opening
9 powder receiving depression
10 plunger
11 blister chamber
12 stop
14, 14' elastic insert with pressure dome
15 storage half shell
16 film hinge
17, 17' de-agglomeration devices
18 ribbing on sidewall
18' dome-shaped projection
19 storage space
20 mouthpiece
21 nose tube
22 outlet wall
31, 41 back wall of the half shells
32, 42 sidewall of the half shells
32' cutout
32" projection
34 thicker wall portion opposite powder receiving depression
100 blister
101 active ingredient depression
102 folded over pulling tab of the cover film
103 positioning opening

What is claimed is:

1. A powder inhaler (1), comprising:
a first half shell and a second half shell (3, 4) that are connected to each other by at least one film hinge (16), the first and second half shells and the at least one hinge formed as one piece, wherein the first and second half shells (3, 4) in a joined arrangement, in which the first and second half shells are folded onto each other, enclose an air inlet area, a powder deposition and release area, and an outlet area through which a fluid path is extending;
wherein at least one of the first and second half shells (3, 4) in the air inlet area comprises at least one air inlet opening (8);
wherein the first half shell comprises one or more powder receiving depressions (9) in the powder deposition and release area, wherein the one or more powder receiving depressions (9) are configured to receive a depression (101) of a blister element (100) dimensioned to be received in the powder inhaler (1), the blister element (100) comprising a support film in which the depression (101) containing at least one active ingredient powder that is inhalable is formed and comprising a cover plate closing off the depression (101);
wherein the outlet area comprises one or more de-agglomeration structures (17, 17') and an outlet for aerosol that is formed by the first and second half shells (3, 4);
wherein the first and second half shells (3, 4) are flat and comprise an elongate substantially rectangular, trapezoidal, drop-shaped or oval base that is rimmed by sidewalls (32, 42) and a wall section (31, 41) that is opposite the outlet;
wherein the at least one air inlet opening (8) is arranged on the wall section (31, 41);
wherein on at least one of the first and second half shells (3, 4) two or more guide webs (6) are provided and extend in a fan shape from the wall section (31, 41) and/or from the sidewalls (32, 42) adjacent to the wall section (31, 41) all the way to the at least one powder receiving depression (9), wherein the guide webs (6) on the at least one of the first and second half shells (3, 4) have a height extending all the way to the other half shell (3, 4) or to the guide webs (6) provided on the other half shell (3, 4), wherein two side by side neighboring guide webs (6) form an air supply channel and delimit the fluid path in the air inlet area, respectively, wherein the air supply channels each comprise a cross-section that is tapering toward the one or more powder receiving depressions (9);
wherein the one or more powder receiving depressions (9) are framed along the fluid path on two sides by guide walls (7) which extend away from the guide webs (6) that are outermost guide webs of the fan shape and lead to the one or more powder depressions (9);
wherein the powder inhaler is further configured such that:
in the powder deposition and release area, the second half shell comprises, at a location which is positioned opposite the one or more powder receiving depressions (9), a plunger (10) that is elastically moveably inserted in the second half shell in the direction toward the one or more powder receiving depression (9), wherein the plunger (10) is a pricker for opening an active ingredient depression (101) of a blister element (100) when inserted into the powder inhaler (1),
and/or
on one of the first and second half shells (3, 4) one of the sidewalls (32, 42) at the level of the one or more powder receiving depressions (9) comprises a cutout (32') having a width and a height corresponding to a width and a height of a blister element (100) dimensioned to be received in the powder inhaler (1), wherein on the sidewall (32, 42) that, in the joined arrangement, is positioned above the cutout (32'), the other one of the first and second half shells (3, 4) that does not have the cutout (32') comprises a projection (32") that closes off the cutout (32') when a blister element (100) is inserted into the powder inhaler (1).

2. The powder inhaler (1) according to claim 1, wherein the powder inhaler (1) is an injection molded part.

3. The powder inhaler (1) according to claim 1, comprising a plurality of the powder receiving depressions, wherein at least one of the air supply channels extends to each one of the powder receiving depressions (9).

4. The powder inhaler (1) according to claim 1, further comprising air swirling structures wherein the air supply channels each have at least one of the air swirling structures arranged therein.

5. The powder inhaler (1) according to claim 4, wherein the air swirling structures each are formed by a plurality of vanes connected to the guide webs (6) and projecting from the guide webs (6) into the air supply channels, respectively.

6. The powder inhaler (1) according to claim 5, wherein the vanes (5) are alternatingly arranged on two oppositely positioned ones of the guide webs (6) and/or on side by side neighboring ones of the guide webs (6), respectively, and form obstacles for an air stream that is flowing along the fluid path.

7. The powder inhaler (1) according to claim 6, wherein the outlet is formed as a mouthpiece or a nose piece.

8. The powder inhaler (1) according to claim 7, wherein the mouthpiece is formed as a spout (20) or the nose piece is formed as a curved nose tube (21).

9. The powder inhaler (1) according to claim 8, wherein at least one of the de-agglomeration structures (17) is formed by webs (17) that extend from oppositely positioned wall sections (22) of the outlet area into the fluid path.

10. The powder inhaler (1) according to claim 9, wherein the webs (17) projecting into the fluid path are alternatingly arranged on the wall sections (22) of the outlet area.

11. The powder inhaler (1) according to claim 1, wherein at least one of the de-agglomeration structures (17') adjoins the powder deposition and release area and is formed by at least one deflection web (17') arranged in one of the first and second half shells (3, 4).

12. The powder inhaler (1) according to claim 11, wherein the at least one deflection web (17') is arranged in the first half shell.

13. The powder inhaler (1) according to claim 1, further comprising an elastic insert to which the plunger (10) is connected, wherein the elastic insert with the plunger is inserted into the second half shell so that the plunger is movable in a direction toward the one or more powder receiving depressions (9).

14. The powder inhaler (1) according to claim 1, wherein the first half shell comprises at least one stop that is provided for framing a blister element (100) when inserted into the powder inhaler (1).

15. The powder inhaler (1) according to claim 1, wherein the first and second half shells (3, 4) have a ribbing (18) at the sidewalls (32, 42) opposite the cutout (32') and the projection (32"), wherein the ribbing (18) is arranged at the level of the one or more powder receiving depressions (9).

16. The powder inhaler (1) according to claim 1, wherein the first half shell has a projection that is configured to engage a corresponding cutout (103) of a blister element (100) when inserted into powder inhaler (1).

17. The powder inhaler (1) according to claim 16, wherein the projection is dome-shaped.

18. The powder inhaler (1) according to claim 1, further comprising at least one third half shell (15) connected by at least one hinge (16) to the first half shell or the second half shell.

19. The powder inhaler (1) according to claim 18, wherein the at least one third half shell (15) is connected to that one of the first and second half shells that does not comprise the at least one air inlet (8).

20. The powder inhaler (1) according to claim 18, wherein the third half shell (15) comprises a base corresponding to a shape of the base of the first and second half shells (3, 4) and having a size configured to store at least one blister element (100) dimensioned to be received in the powder inhaler (1).

21. The powder inhaler (1) according to claim 18, wherein the third half shell (15) comprises locking means for locking the third half shell (15) on at least one of the first and second half shells (3, 4).

22. The powder inhaler (1) according to claim 1, comprising locking means for locking the first and second half shells (3, 4) to each other.

23. A powder inhalation set (1, 100) comprising a powder inhaler (1) according to claim 1 and a blister element (100) dimensioned to be received in the powder inhaler (1), wherein the blister element (100) comprises a support film with at least one depression (101) that is configured to receive at least one active ingredient powder that is inhalable, and a cover plate that closes off the at least one depression (101), wherein the at least one depression (101) of the blister element (100) in size and position is formed to be received in the powder receiving depression (9) of the powder inhaler (1).

24. The powder inhalation set (1, 100) according to claim 23, wherein, for opening the depression (101),
the cover plate is designed to be removable from the support plate through the cutout (32') in the sidewall (32, 42) of the powder inhaler at the level of the powder receiving depression (9) of the powder inhaler,
and/or
the cover plate is penetrable by the plunger (10), which is arranged in the second half shell (3, 4) of the powder inhaler (1) opposite the one or more powder receiving depression (9) and is elastically moveable.

* * * * *